United States Patent
Willard et al.

[11] Patent Number: 5,831,184
[45] Date of Patent: Nov. 3, 1998

[54] SAMPLE HOLDER FOR A SAMPLE TO BE SUBJECTED TO RADIATION ANALYSIS

[75] Inventors: Nicolaas Petrus Willard; Pieter K. De Bokx, both of Eindhoven, Netherlands

[73] Assignee: U.S. Philips Corporation, New York, N.Y.

[21] Appl. No.: 710,626

[22] Filed: Sep. 20, 1996

[30] Foreign Application Priority Data

Sep. 22, 1995 [EP] European Pat. Off. .............. 95202561

[51] Int. Cl.$^6$ ................................................... G01N 37/00
[52] U.S. Cl. ..................... 73/864.91; 356/244; 356/246; 250/440.11
[58] Field of Search ................................ 73/864.91, 863; 356/244, 246; 378/208; 250/428, 440.11

[56] References Cited

U.S. PATENT DOCUMENTS

| | | | |
|---|---|---|---|
| 4,473,457 | 9/1984 | Columbus | 73/864.91 |
| 4,957,582 | 9/1990 | Columbus | 73/864.91 |
| 5,544,218 | 8/1996 | Turner et al. | 73/864.91 |

FOREIGN PATENT DOCUMENTS

| | | | |
|---|---|---|---|
| 249736 | 9/1992 | Japan | 73/864.91 |
| 5312698A | 11/1993 | Japan . | |

*Primary Examiner*—Hezron E. Williams
*Assistant Examiner*—Nashmiya S. Fayyaz
*Attorney, Agent, or Firm*—Anne E. Barschall

[57] ABSTRACT

For TXRF (Total Reflection XRF) or GEXRF (Grazing Emission XRF) a very flat sample surface and a suitably defined region in which the sample material is present are often required. Both requirements can be satisfied by means of a (preferably synthetic) sample carrier on which a first region which has a small liquid contact angle is surrounded by a second region having a large contact angle. When applied in the first region, a droplet of solvent containing the sample material will completely wet said region, whereas the second region will not be wetted. As the solvent evaporates, the boundary of the droplet does not retreat but the first region remains fully wetted, resulting in uniform coverage of this region by sample material and also in a suitably defined sample spot.

8 Claims, 1 Drawing Sheet

SAMPLE HOLDER FOR A SAMPLE TO BE SUBJECTED TO RADIATION ANALYSIS

BACKGROUND OF THE INVENTION

1. Field of the Invention

The invention relates to a sample holder for a sample to be subjected to radiation analysis, comprising a carrier for the material to be examined.

2. Related Art

A sample carrier for such a sample holder is known from Japanese patent document No. 5-312698.

Methods are known for the analysis of materials in which a sample of the relevant material is exposed to radiation (for example, X-rays) and in which the incident radiation produces radiation in the sample which is characteristic of the composition and the structure of the material to be examined. When use is made of X-rays, this analysis method is the known as X-ray Fluorescence spectrometry or XRF. Special versions of XRF are those where the X-rays are incident on the sample at a grazing angle (i.e. at an angle which is smaller than the angle for total X-ray reflection, the so-called limit angle), called Total Reflection XRF or TXRF, or where the fluorescence radiation generated in the sample is taken off at an angle which is smaller than the limit angle (Grazing Emission XRF or GEXRF). Both analysis methods are based on the fact that only the fluorescence radiation emanating from the upper few atomic layers is detected, so that a signal-to-noise ratio is obtained which is substantially better than in the case of X-ray fluorescence with non-total reflection. As a result, very low concentrations of elements can be detected by means of TXRF and GEXRF.

Because said TXRF and GEXRF analysis techniques utilize very small angles of incidence or emission (of the order of magnitude of 0.5° or less), severe requirements are imposed as regards the smoothness of the specimen surface. This means that in the case of small quantities of the material to be examined, severe requirements are imposed also as regards the smoothness of the surface of the sample carrier. Small inhomogeneities in the surface to be examined may lead to deviating results. Therefore, there is a need for a sample carrier having a flat and smooth surface which enables analysis techniques utilizing radiation at very small angles.

The sample holder described in the cited Japanese patent document comprises a sample carrier which is made of polyvinyl. This material is sufficiently flat and smooth for the described analysis techniques. Materials to be studied are often applied to the sample carrier as a solution in a liquid, notably water; the liquid then evaporates, thus leaving behind the dissolved material in the solid condition. For the reasons stated above it is desirable that the material left behind forms a smooth, homogeneous surface. A sample carrier made of a synthetic material has the drawback that because of the wetting properties of synthetic materials the liquid droplets deposited thereon do not dry uniformly. As a result, drying of the solvent often fails to produce the desired uniform distribution of the sample material. It is a further drawback that the delimitation of the sample material left behind is not reproducible, so that it may very well happen that a part of the material is not irradiated when placed in the irradiation apparatus. This is a drawback in the case of quantitative measurements where one is interested in the quantity of a given material in a given quantity of solvent.

SUMMARY OF THE INVENTION

It is an object of the invention to provide a sample holder of the kind disclosed in the introductory part of claim 1 which enables uniform drying of a solution with a sample material in a given, constant region. To this end, the sample holder in accordance with the invention is characterized in that the surface of the carrier which comes into contact with the material to be examined comprises a first surface portion having a liquid contact angle which is smaller than that of a second surface portion of the carrier. The contact angle of the first surface portion may be chosen so that complete wetting by the solvent occurs in said region. During evaporation of the solvent, this region remains uniformly wetted because the wetting boundary does not retreat. Therefore, there will be no drying spots causing inhomogeneities.

An embodiment of the sample holder in accordance with the invention is characterized in that the surface of the carrier consists of one material and that the liquid contact angle of the first surface portion is realized by modification of the structure of the material of the first surface portion. The sample carrier can thus be readily manufactured by utilizing of a surface working operation.

Another embodiment of the sample holder in accordance with the invention is characterized in that the carrier is made of a synthetic material. Synthetic materials are excellently suitable for realizing a reduction of the contact angle by means of a surface working operation. The modification of the structure can be realized notably by exposure to ultraviolet radiation. The polymer nature of the synthetic material is then slightly disturbed, resulting in the desired structure modification.

In a further embodiment of the invention, the exposure to ultraviolet radiation has taken place in the presence of oxygen. The reaction of the synthetic material exposed to ultraviolet light is accelerated by the presence of oxygen, which itself is rendered more reactive by exposure to ultraviolet radiation.

Another embodiment of the invention is characterized in that the liquid contact angle of the second surface portion is realized by depositing a layer of a material having a liquid contact angle which is larger than that of the first surface portion on the second surface portion. In given circumstances it may be attractive to utilize a material having a comparatively small contact angle for a given solvent and to impart subsequently a larger contact angle for the relevant material to the region which is not to be wetted. The effect thus achieved is in principle the same as that obtained by reducing the contact angle for the region to be wetted. This material is preferably a wax-like material which can be readily applied by rubbing or stamping.

BRIEF DESCRIPTION OF THE DRAWING

These and other aspects of the invention will be apparent from and elucidated with reference to the embodiments described hereinafter.

In the drawings.

DETAILED DESCRIPTION OF THE PREFERRED EMBODIMENTS

Figure 1:
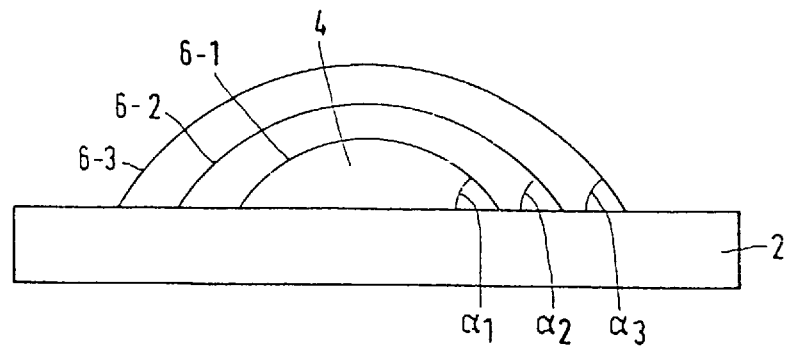
FIG. 1 is a sectional view of a prior art sample carrier with different stages of a drying droplet in which a material to be examined is dissolved.

FIG. 1 shows a sample carrier 2 which is made of a synthetic material, for example polyvinyl. This material is sufficiently flat and smooth for the TXRF and GEXRF analysis techniques but, like most synthetic materials, has the drawback of a comparatively large liquid contact angle, notably for water. On the sample carrier there is deposited a droplet 4 of a solvent, for example water, in which the material to be examined has been dissolved. Evaporation of the solvent leaves behind the material to be examined. For the TXRF and GEXRF analysis techniques the material left behind must have a smooth surface; however, due to the comparatively large liquid contact angle, drying spots occur which disturb the smoothness and regularity of the surface. The Figure shows three stages in the evaporation process of the solvent droplet 4.

When a droplet of solvent is applied to the surface of the sample carrier, a liquid region 6-1 having a comparatively large contact angle $\alpha_1$ (for example, 70°) will develop on the non-treated synthetic material. As the droplet evaporates, the boundary of the droplet retreats via the stages 6-2 and 6-3, the comparatively large liquid contact angle being maintained. The values of $\alpha_1$, $\alpha_2$ and $\alpha_3$ then remain equal.

Figure 2:
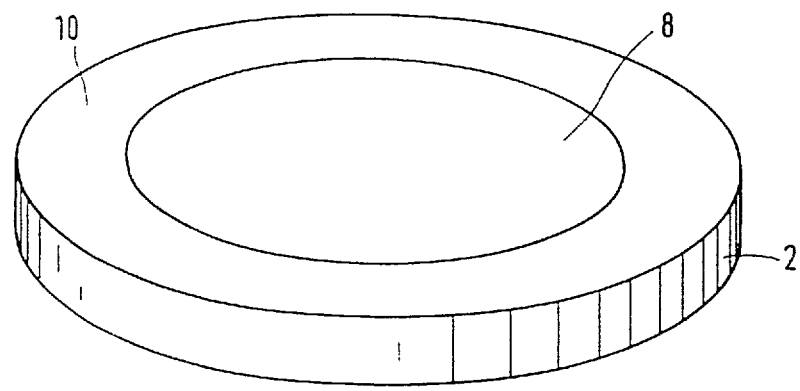
FIG. 2 is a perspective view of a sample carrier in accordance with the invention, comprising a central region having a comparatively small liquid contact angle and an outer region having a comparatively large liquid contact angle.

FIG. 2 is a perspective view of a sample carrier 2 on the surface of which there is formed a region 8 which has been worked in such a manner that therein the liquid contact angle is substantially smaller than in the remaining region 10. However, the region 10 can alternatively be worked in such a manner that the liquid contact angle in this region is substantially larger than that in the remaining region 8, as will be described in detail with reference to FIG. 3.

Figure 3:
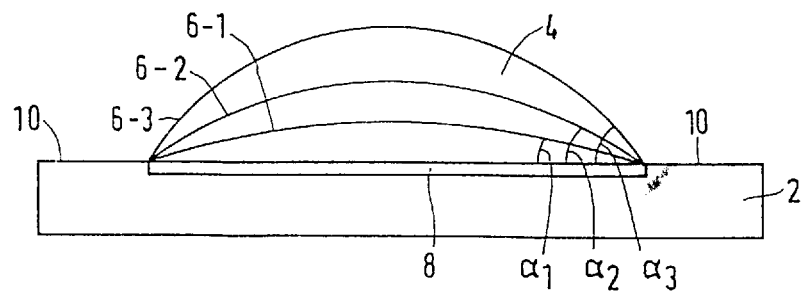
FIG. 3 is a sectional view of a sample carrier in accordance with the invention with different stages of a drying droplet in which a material to be examined is dissolved.

FIG. 3 is a sectional view of the sample carrier, comprising a region 8 having a comparatively small liquid contact angle and a region 10 having a comparatively large liquid contact angle. The region 8 can be realized in various ways, for example by activation by means of ultraviolet (UV) light, by means of UV light in combination with oxygen, by means of a corona discharge or a plasma, or chemically. These treatments are known per se and can be applied to a variety of synthetic materials such as polycarbonate (tradename Lexan), polymethyl methacrylate (tradename Perspex) or polypropylene.

In an embodiment of the invention a sample carrier of polycarbonate is treated by means of a combination of oxygen ($O_2$) and UV light. In a first space oxygen is exposed to UV light of a wavelength of 185 nm, thus forming ozone ($O_3$). The polycarbonate sample carrier is introduced into a second space in which the region 10 which is not to be subjected to the treatment is masked by means of a mask. In the second space, moreover, the gas mixture treated in the first gas space is admitted, after which irradiation by UV light of a wavelength of 254 nm takes place therein. During this irradiation there are formed free oxygen atoms which react with the polymer molecules of the polycarbonate. As a result, the structure of this material is modified in such a manner that the liquid contact angle becomes substantially smaller, even as small as approximately 0°.

Another embodiment of the invention utilizes a corona discharge in air of approximately atmospheric pressure. The carrier of synthetic material is then introduced into the corona discharge, the parts which are not to be treated again being masked.

A plasma treatment, can also be used. Radio frequency waves or waves of microwave frequency are then used to produce a plasma of a gas. For the gas use can be made of, for example nitrogen ($N_2$), oxygen ($O_2$), carbon dioxide ($CO_2$) or ammonia gas ($NH_3$) at a pressure of the order of magnitude of 0, −1 mbar. The sample carrier of synthetic material is introduced into the plasma, the parts which are not to be treated again being masked.

A chemical treatment can also be applied. The carrier of synthetic material is then introduced into water-diluted sulphuric acid ($H_2SO_4$) in which chromium oxide ($Cr_2O_3$) has been dissolved. The parts which are not to be treated are again masked.

In all cases the treatment time should be experimentally determined; this can be readily performed because the criterion in respect of effectiveness of the treatment is the occurrence of a sufficiently small liquid contact angle.

Another embodiment of the invention utilizes a sample carrier having a comparatively small liquid contact angle. For this purpose a synthetic material treated by means of one of the above methods can be chosen, or a material inherently exhibiting a small contact angle. A surface region 10 of this sample carrier is then formed by stamping or rubbing on a material having a comparatively large liquid contact angle, such as bee wax or silicon wax. Such layers need have a very small thickness only, for example a few nanometers, so that only a very small quantity of this material is required.

Even though only water has been mentioned as the solvent for the material to be examined, to those skilled in the art it will be evident that other solvents can also be used, for example alcohol (ethanol). In that case a different synthetic material may have to be chosen so as to form a region having a large liquid contact angle, for example polytetrafluoroethylene (tradename Teflon) or silicon polymers.

We claim:

1. A sample holder for a sample to be subjected to radiation analysis, the sample holder comprising a carrier for a sample of a material to be examined, the carrier including a free surface arranged to come into contact with the material to be examined, the surface including first and second surface portions having respective first and second liquid contact angles, the first liquid contact angle being smaller than the second liquid contact angle, the second surface portion surrounding the first surface portions, wherein the free surface is substantially flat so as to be suitable for bearing samples to be subjected to grazing x-ray analysis.

2. A sample holder as claimed in claim 1, further characterized in that the surface of the carrier originally consists of one material and that the liquid contact angle of the first surface portion is realized by subsequent modification of the structure of part of the one material.

3. A sample holder as claimed in claim 1, further characterized in that the carrier is made of a synthetic material.

4. A sample holder as claimed in claim 2, further characterized in that the modification of the structure is realized by exposure to ultraviolet radiation.

5. A sample holder as claimed in claim 4, further characterized in that the exposure to ultraviolet radiation has taken place in the presence of oxygen.

6. A sample holder as claimed in claim 1, further characterized in that the liquid contact angle of the second surface portion is realized by depositing a layer of a material having a liquid contact angle which is larger than that of the first surface portion on the second surface portion.

7. A sample holder as claimed in claim 6, further characterized in that the material having a liquid contact angle larger than that of the first surface portion is a wax-like material.

8. A sample holder as claimed in claim 2, further characterized in that the carrier is made of a synthetic material.

* * * * *